United States Patent [19]

Eswara et al.

[11] Patent Number: 5,707,872
[45] Date of Patent: Jan. 13, 1998

[54] NICOTINE AND/OR NICOTINE METABOLITE DETECTION

[75] Inventors: Amruta R. Eswara, Beverly; Neal Muni, Reading, both of Mass.

[73] Assignee: DynaGen, Inc., Cambridge, Mass.

[21] Appl. No.: 474,534

[22] Filed: Jun. 7, 1995

Related U.S. Application Data

[63] Continuation of Ser. No. 279,619, Jul. 25, 1994, abandoned, which is a continuation of Ser. No. 137,687, Oct. 15, 1993, abandoned, which is a continuation of Ser. No. 862,051, Apr. 2, 1992, abandoned.

[51] Int. Cl.[6] .................................................. G01N 33/493
[52] U.S. Cl. ........................ 436/96; 436/98; 436/164; 436/816; 422/58
[58] Field of Search .................... 422/56–58; 436/63, 436/96, 98, 164, 816

[56] References Cited

U.S. PATENT DOCUMENTS 4,160,008  7/1979  Fenocketti et al.
4,548,906  10/1985  Sekikawa et al. .................... 422/58

OTHER PUBLICATIONS

Smith Celia L. et al., The Analyst, vol. 112, No. 11, Nov. 1987, pp. 1515–1518, "Evaluation of Diethylthiobarbituric Acid as a Spectrophotometric Reagent for Tobacco Alkaloids".

Kilburn et al., American Review of Respiratory Disease, vol. 106, No. 6, Dec. 1972, pp. 923–924, "Reagent–Impregnated Paper Strip for Detection of Metabolic Products of Isoniazid in Urine".

Barlow Robet D. et al., Clinica Chimica Acta, vol. 165, No. 1, May 1987, pp. 45–52, "The direct barbituric acid assay for nicotine metabolites in urine: a simple colorimetric test for the routine assessment of smoking status and cigarette smoke intake".

Peach Hedley et al., Thorax, vol. 40, No. 5, May 1985, pp. 351–357, "A simple, inexpensive urine test of smoking".

Langone, J., et al., "Monoclonal Antibody ELISA for Continine in Saliva and Urine of Active and Passive Smokers", Jrnl. of Immuno Methods, 114:73–78 (1988).

Langone, J., et al., "Nicotine and Its Metabolites. Radioimmunoassays for Nicotine and Cotinine", Biochem. 12:24 (1973).

Rubin, S., et al., "Determination of Blood Plasma Levels of Hydrazine Derivatives of Isonicotinic Acid", Dis. Chest., 21:439 (1952).

Belles, Q., et al., "A Sensitive Filler Paper Spot Test for the Detection of Isoniasid (INH) Metabolites in Urine", Med. Jrnl. of Australia, 2:588 (1962).

Kasik, J.E., et al., "A simple Test to Determine Whether a Patient is taking Isoniazid", Amer. Rev. Resp. Dis., 85:282 (1962).

Kilburn, J., et al., "Reagent–Impregnated Paper Strips for Detection of Niacin", Amer. J. Clinical. Path., 38:530 (1968).

Kilburn, et al., "Reagent–Impregnated Paper Strip for Detection of Isoniazed in Urine", Rev. Resp. Dis., 106:923 (1972).

(List continued on next page.)

*Primary Examiner*—Lyle A. Alexander
*Attorney, Agent, or Firm*—Wolf, Greenfield & Sacks, P.C.

[57] ABSTRACT

A solid phase capable of detecting the presence of nicotine and/or nicotine metabolites is described. The solid phase is impregnated with assay reagents including a color determinant, a buffer, a cyanogen releasing agent and a cyanogen halide forming agent. The solid phase provides a means whereby unprocessed urine samples over a wide range of different pH values can be tested for the presence of nicotine and/or nicotine metabolites. The assay results may be determined by direct visualization of the color of the solid phase. Also described are methods of preparing and using the solid phase, and kits containing the solid phase.

30 Claims, 3 Drawing Sheets

OTHER PUBLICATIONS

Stanley, J., et al., "An Investigation of Dapsone Compliance using an Isoniazid–marked Formulation", Leprosy Review, 54:317 (1983).

Peach, et al., "Simple, Inexpensive Urine Test of Smoking", Thorax, 40:351 (1985).

Barlow, R., et al., "The Direct Barbituric Acid Assay for Nicotine Metabolites in Urine: a simple Colorimetric Test for the Routine Assessment of Smoking Status and Cigarette Smoke intake", Clinica. Chimica. Acta., 165:45 (1987).

Kolonen, S., et al., "Assessment of the Automated Colorimetric and the high–performance liquid Chromatographic methods for Nicotine intake by Urine Samples of Smokers Smoking low–and medium–yield Cigarettes", Clinica. Chimica. Acta. 170:255 (1987).

Kullberg, M. et al., "Studies on the Single Extraction of Amphetamine and Phenobarbital from Urine[1] Using XAD–2 Resin", Biochem. Med., 7:323–335 (1973).

Mule, S.J., et al., "Routine Identification of Drugs of Abuse in Human Urine", Jrnl. of Chrom., 63:289–301 (1971).

Miller, W.L., et al., "Studies on the Quantitative Extraction of Morphine from Urine[1] Using Nonionic XAD–2 Resin",. Biochem. Med. 7:145–158 (1973).

Kullberg, M.P., et al., "Studies on the Use of XAD–2 Resin for Detection of Abused Drugs in Urine", Clinic. Chem. 20:2, 177 (1974).

Watson, L, "Rapid Analysis of Nicotine and Cotinine in the Urine of Smokers by Isocratic High–performance Liquid Chromatography", Jrnl. Chroma. 143:203–206 (1977).

Kyerematen, G., et al., "Smoking–induced changes in Nicotine Disposition: Application of a new HPLC Assay for Nicotine and its Metabolites", Clin. Pharmacol. Ther., 32:769 (1982).

Jacob, P., et al., "Improved Gass Chromatographic Method for the Determination of Nicotine and Cotinine in Biologic Fluids", Jrnl. of Chroma. 222:61–70 (1981).

Hengen, N., et al., "Gas–Liquid Chromatographic Determination of Nicotine and Cotinine in Plasma", Clin. Chem., 24/1:50–53 (1978).

Feyerabend, C., "Rapid Gas–Liquid Chromatographic Determination of Cotinine in Biological Fluids", Analyst, 105:998 (1980).

Knight, G., et al., "Improved [125]I Radioimmunoassay for Cotinine by Selective Removal of Bridge Antibodies", Clin. Chem. 31/1:118–121 (1985).

Puhakainen, E., "An automated Colorimetric Assay for Urine Nicotine Metaboites: a suitable alternative to Continine Assays for the Assessment of Smoking Status", Clinica. Chimica. Acta., 170:255–262 (1987).

Kraus, P., et al., "Paper Strip Urine Test for Checking the Intake of Isoniazid", Tubercle, Lond., 46:206 (1965).

Yamasaki, E., "Concentration of Mutagens from Urine by Adsorption with the Nonpolar Resin XAD–2: Cigarette Smokers have Mutagenic Urine", Proc. Natl. Acad. Sci. USA (1977).

Henderson, W., "The Development and Use of the Potts–Cozart Tube Test for the Detection of Isoniazid (INH) Metabolites in Urine", Jrnl. Arkansas Med. Soc., (1988).

Young, W., et al., "Development of a Paper Strip Test for Detection of Niacin Produced by Mycobacteria", Applied Microbiology, 20/6:939–945 (1970).

Watts, R., et al., "Continine Analytical Workshop Report: Consideration of Analytical Methods for Determining Cotinine In Human Body Fluids as a Measure of Passive Exposure to Tobacco Smoke", Enviro. Health Persp., 84:173–182 (1990).

Bjercke, R., et al., "Stereospecific Monoclonal antibodies to nicotine and cotinine and their use in enzyme–linked immuno–sorbent assays", Jrnl. Immuno. Methods, 90:203–213 (1986).

Jacob, P., et al., "Oxidative Metabolism of Nicotine In Vivo", Effects of Nicotine on Biological Systems (1991).

Parviainen, M., et al., "Nicotine Metabolites in the Urine of Smokers", Jrnl. of Chromo. 525:193–202 (1990).

Kyerematen, G., et al., "Disposition of Nicotine and Eight Metabolites in Smokers and Nonsmokers: Identification in Smokers of Two Metabolites that are no longer lived than Cotinine", Clin Pharmacol. Ther., 641–651, (1990).

Jacob, N., et al., "Measurement of Urinary Tobacco Markers in a Smoking–Cessation Program", Clinical Chemistry, 37/9:1655 (1991).

Takanashi, S., et al., "Adriamycin Metabolism in Man. Evidence From Urinary Metaboites", Drug Metabolism and Disposition, 4/1: 79, (1976).

Burnham, A.K., et al., "Identification and Estimation of Neutral Organic Contaminants in Potable Water", Institute for Atomic Research and Dept. of Chem.

Cox P. et al., "Novel Metabolic Products of Cyclophosphamide in Human Urine", Biochem. Pharma., 24:1233–1235, (1975).

NICOTINE
Fig. 1a

NICOTINE - 1' - N - OXIDE
Fig. 1b

NOR - NICOTINE
Fig. 1c

COTININE
Fig. 1d

3 - HYDROXY - COTININE
Fig. 1e

COTININE - N - OXIDE
Fig. 1f

NOR - COTININE
(DES METHYL COTININE)
Fig. 1g

3 - HYDROXY - COTININE
GLUCURONIDE
Fig. 1h

3 - PYRIDYL - CARBINOL
Fig. 1i

3 - PYRIDYL ACETIC ACID
Fig. 1j

DEMETHYL - COTININE $\Delta^{T3'}$ - ENAMINE
Fig. 1k

NICOTINE AND/OR NICOTINE METABOLITE DETECTION

This application is a continuation of application Ser. No. 08/279,619, filed Jul. 25, 1994, now abandoned which is a File Wrapper Continuation of prior application Ser. No. 08/137,687, filed on Oct. 15, 1993, now abandoned which is a File Wrapper Continuation of prior application Ser. No: 07/862,051, filed Apr. 2, 1992 now abandoned.

BACKGROUND

Nicotine use such as by cigarette smoking is a major public health problem. Clinicians and epidemiologists often need an accurate assessment of whether and to what extent a person smokes or otherwise uses nicotine. Relying upon self-reporting by nicotine users regarding their nicotine habits is often inaccurate. In addition, clinicians and epidemiologists may require information concerning inhalation of secondary smoke by non-smokers as well as concerning other passive exposure to nicotine as a result of environmental conditions. Various assays have been developed to independently obtain such information.

High performance liquid chromatography (HPLC) has been used to specifically determine the level of cotinine, a nicotine metabolite, in the urine of subjects. (Watson, J. D., *J. Chromatogr*, 143:203 (1977); Kyerematen, G. A., *Clin. Pharmacol. Ther.*, 32:769 (1982)). Cotinine levels also have been tested using gas chromatography (GC). (Jacob, P. et al., *J. Chromatogr.* 222:61 (1981); Hengen, N. and Hengert, M., *Clin. Chem.* 24:50 (1978); Feyerabend, C. and Russell, M., *Analyst* 105:993 (1980)). Both of these methods require expensive equipment, trained personnel, and are very time consuming. Radioimmunoassays (RIA) (Langone, J., et al., *Biochemistry* 12:5025 (1973); Knight, G. et al. *Clin. Chem.* 31:118 (1985)), and enzyme linked immunoassays (ELISA) that measure cotinine have also been developed. (Langone et al. *J. Immunol. Methods* 114:73 (1988)). Such assays also require special equipment, trained personnel and special reagents.

Various assays for isoniazid, a drug used in the treatment of tuberculosis, have been reported. Originally, Rubin et al. (*Dis. Chest.* 21: 439 (1952)) developed a method for the identification of isoniazid metabolites using cyanogen bromide. Nielsch and Giefer (*Arzneimittel-Forschung* 9: 636 (1959); *Arzneimittel-Forschung* 9: 700 (1959)), using chloramine-T and potassium cyanide, developed an assay by which the pyridine ring of isoniazid metabolites is split by cyanogen chloride and condensed with barbituric acid to give a blue to purple color. This was modified by Belle and Littleman (*Med. J. Aust.* 2: 588 (1962)) for a quantitative determination of isoniazid metabolites, and was later modified by Kasik et al. to be used as a qualitative liquid spot test (*Amer. Rev. Resp. Dis.* 85: 282 (1962)). Kilburn and Kubica (*Amer. J. Clinical Pathology* 38: 530 (1968)) modified this test system to enable detection of niacin, utilizing a strip that was impregnated with p-amino salicylic acid, potassium thiocyanate in citric acid and chloramine-T. Subsequently, the reagent impregnated paper strip method was adapted for the detection of isoniazid metabolites. (Kilburn et al., *Amer. Rev. Resp. Dis.* 106: 923 (1972)). This paper strip system contained barbituric acid, potassium thiocyanate in citric acid, and chloramine-T. Presence of isoniazid metabolites gave a blue to purple color in this assay.

Stanley et al. (*Leprosy Review*, 54: 317 (1983)) describe a liquid assay in the above isoniazid reaction wherein an orange color was observed when the urine of smokers who were not on isoniazid was tested. Peach et al. (*Thorax* 40: 351 (1985)) tested this reaction as a possible useful assay for the detection of nicotine metabolites in smokers. They reported results of assays performed in liquid, using the reagents diethyl thiobarbituric acid or barbituric acid, potassium cyanide, chloramine-T and acetate buffer. This barbituric acid liquid assay method was modified for use with microtitre plates for screening large numbers of samples. (Barlow et al. *Clinica Chimica. Acta.*, 165:45 (1987)). A microtitre plate reader was needed to measure the absorbance of each well. This assay also has been adapted for use with an autoanalyzer. (Puhakainen et al., *Clinica. Chimica. Acta.* 170: 255 (1987); Kolonen and Puhakainen, *Clinica. Chimica. Acta.* 196: 159 (1991)). The above-described liquid assays required sequential addition of reagents and sometimes waiting periods for the user between the sequential additions.

SUMMARY OF THE INVENTION

The present invention provides a detection system which is a solid phase, one-step assay useful in detecting the presence of nicotine and/or nicotine metabolites. The detection system of the present invention is reliable, easy, quick, and can be carried out by personnel with little or no training. No solutions of liquid reagents are required as the invention is a completely self-contained solid phase. No analyzing equipment is required, as the assay results may be determined by direct visualization of the color of the solid phase. Moreover, this invention permits testing of unprocessed urine samples that have a wide range of different pH values.

The detection system is a solid phase containing the required reagents for the nicotine and/or nicotine metabolite assay. These reagents include a color determinant, a buffer, a cyanogen releasing agent and a cyanogen halide forming agent. Preferably, these reagents are arranged in a certain sequence on the solid phase. The buffer permits detection of nicotine and/or nicotine metabolites from samples having a wide range of different pH values. This invention enables not only the detection of nicotine and/or nicotine metabolites from unprocessed urine samples of active nicotine users, but also enables detection of nicotine and/or nicotine metabolites from processed urine samples of nonsmokers passively exposed to nicotine.

The present invention also pertains to a method for detecting nicotine and/or nicotine metabolites by immersing a solid phase containing the assay reagents into a liquid test sample and observing any color change on the solid phase. Preferably, the intensity of the resultant color is compared to at least one standard in which a known quantity of nicotine and/or nicotine metabolites has been assayed. For example, one standard may be selected to correspond to levels of nicotine and/or nicotine metabolites from a urine sample of a heavy smoker, another standard may be selected to correspond to levels from a light smoker, and another standard may be selected for use in assays detecting nicotine resulting from passive smoke, e.g. 100–300 ng/ml.

The present invention also pertains to a method of differentiating between smokers and nonsmokers or differentiating between light and heavy smokers. These methods involve obtaining biological samples from individuals and contacting these samples with the solid phase containing the reagents as described above. In these methods, either the presence or absence of the formation of color is detected as an indication of the individual being a smoker or nonsmoker or the intensity of the color is observed as an indication of an individual being a light or heavy smoker. The solid phase detection system of this invention also may be used in a method for determining whether an individual has been exposed to secondary or passive smoke. Preferably, in this method, the sample is concentrated prior to contacting it with the above-described solid phase.

The present invention also pertains to a method for preparing a solid phase for detecting nicotine and/or nicotine metabolites. This method includes applying the assay reagents to the solid phase and drying the solid phase. For example, reagents may be applied by adsorbing them onto the solid phase. Preferably, these reagents are arranged in a certain sequence on the solid phase. The dried solid phase preferably is then packaged in a moisture proof material.

The present invention further pertains to a kit useful for detecting nicotine and/or nicotine metabolites. The kit contains a packaged solid phase with the assay reagents already applied onto it. The kit also contains instructions providing information to the user regarding the use of the solid phase for detecting nicotine and/or nicotine metabolites. Preferably, the kit also contains at least one standard against which the color intensity of the test assay can be compared.

It is an object of the invention to differentiate active nicotine users from those who do not use nicotine.

It is another object of the invention to differentiate heavy users of nicotine from light users.

It is yet another object of the invention to detect passive exposure to nicotine such as by secondary smoke inhalation.

It is yet another object of the invention to detect extremely low levels of nicotine and/or its metabolites.

It is yet another object of the invention to simultaneously test for the presence of the entire family of nicotine and/or nicotine metabolites.

It is yet another object of the invention to detect nicotine and/or nicotine metabolites without the use of any instruments.

It is yet another object of the invention to provide a colorimetric assay system whereby the presence of nicotine and/or nicotine metabolites can be determined visually.

It is yet another object of the invention to provide an assay system whereby the presence of nicotine and/or nicotine metabolites can be determined in a short period of time.

It is yet a further object of the invention to provide an assay system whereby the presence of nicotine and/or nicotine metabolites can be determined by people with little or no training.

It is yet another object of the invention to provide an assay system whereby the presence of nicotine and/or nicotine metabolites can be detected in unprocessed urine.

Still another object of the invention is to provide an assay system which can be easily performed in a physician's office or in field studies.

DETAILED DESCRIPTION

The present invention pertains to a detection system for detecting nicotine and/or nicotine metabolites. The detection system includes a solid phase containing assay reagents including a color determinant, a buffer, a cyanogen releasing agent and a cyanogen halide forming agent.

The term solid phase is intended to include any solid material that is capable of binding the assay reagents and allowing contact of these reagents with a test sample via capillary action. Examples of solid phases include paper, porous membranes, capillary tubes, resin bed (ionic and non-ionic type columns) and the like. The preferred solid phase is paper. Examples of paper which may be used in this invention include cellulose, fiberglass and tuff glass. The preferred paper is cellulose. The most preferred paper is 100% cellulose (Absorbant Paper Grade #222; Ahlstrom Filtration Inc., Mount Holly Springs, Pa.).

The solid phase is selected for various functions. The solid phase may be adapted to bind reagents that are applied to the solid phase in solutions. Preferably, the solid phase is adapted to permit movement of liquid through the solid phase by capillary action. A porous solid phase will capture and bind the assay reagents onto the solid phase, and also is adapted to facilitate movement of the reagents through the solid phase by capillary action. The solid phase is selected based on its capacity to hold the reagent volumes applied and on its capillary action properties.

The solid phase can be of any size or shape that will retain the volumes and concentrations of the applied assay reagents. Preferably, the solid phase is flat. Also, preferably, the solid phase is of a sufficient size to allow retention of the multiple assay reagents without overlap between reagents. The solid phase also preferably is of a size and shape that is convenient for immersing a liquid contacting end into a liquid test sample. Also, preferably, the size and shape of the solid phase is large enough to contain sufficient concentrations of reagents so as to permit effective visualization of any color that is formed as an end product of the reaction assay on the solid phase. Examples of shapes which can be used are rectangles, squares, ovals, circles and the like. The preferred solid phase is in the shape of a rectangular strip. The most preferred solid phase is a strip that is on the order of 0.5×7.5 centimeters. Also, preferably, the strip is labelled in some manner to demark the top or bottom of the strip in the embodiment of the invention where the assay reagents have been applied to the strip so that they are arranged in a specific sequence to optimize formation of the colored end product.

The term nicotine and/or nicotine metabolites is intended to include nicotine and derivatives of nicotine that are produced as a result of consumption, e.g., smoking, chewing, inhalation, transdermal delivery, or exposure to a nicotine-containing material or as a result of environmental exposure. Since different people metabolize nicotine at different rates, testing for the presence of any one metabolite of nicotine may not accurately reflect the level of nicotine consumed by an individual. This invention provides a diagnostic assay which detects the presence of nicotine and/or a family of nicotine metabolites, by recognizing the pyridine ring of nicotine and its metabolites. It is the total mix of nicotine and its metabolites which is determinative of the intensity of color formation in the reaction assay of this invention. Examples of nicotine and/or nicotine metabolites which are detected in this invention include nicotine, nicotine -1'-N-oxide, nor-nicotine, cotinine, 3-hydroxy-cotinine, cotinine-N-oxide, nor-cotinine (des methyl cotinine), 3-hydroxy-cotinine glucuronide, 3-pyridyl-carbinol, 3-pyridyl acetic acid and demethyl-cotinine Δ 2'3'-enamine. FIG. 1 depicts the structures of some of the nicotine metabolites.

The presence of nicotine and/or nicotine metabolites in any liquid sample can be assayed using this invention. The liquid sample can be any liquid susceptible to containing nicotine and/or nicotine metabolites. The sample may serve as a carrier for at least a portion of reagents on the strip allowing them to come into contact with one another such that a reaction occurs. The sample may be unprocessed or processed depending on the sample selected and the amount of nicotine or nicotine metabolite present in the sample. Processing of a sample may include concentration, pH adjustment, filtration, centrifugation, extraction, and the like. These liquid samples may be biological samples or non-biological samples. An example of a nonbiological liquid is contaminated drinking water. Examples of biological liquid samples include human or animal urine, blood, plasma, serum and saliva. The preferred sample is urine. The most preferred sample is unprocessed urine. In particular, the assay can be used to test the urine of a person or animal (a "subject"). Nicotine and nicotine metabolites can be present in the urine of a subject as a result of that subject actively using nicotine, such as by smoking, chewing or otherwise ingesting a nicotine-containing material, or passively, as a result of a subject inhaling smoke produced for example by a different subject smoking nicotine-containing material or by drinking water that is contaminated with nicotine. In the case of passive smokers where nicotine and metabolite levels are low, concentration prior to measuement is preferred.

Figure 1A:
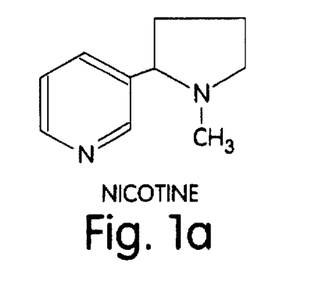
FIG. 1 depicts known human metabolites of nicotine.
Figure 1B:
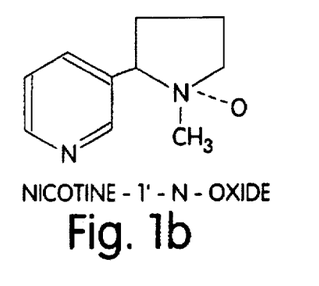
Figure 1C:
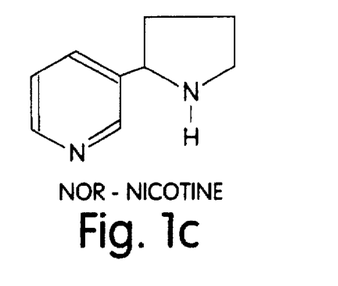
Figure 1D:
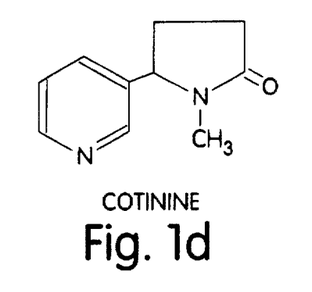
Figure 1E:
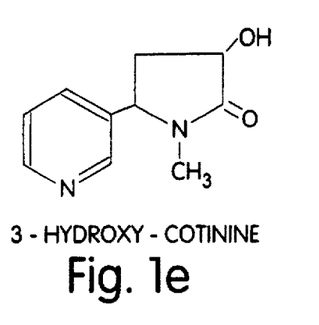
Figure 1F:
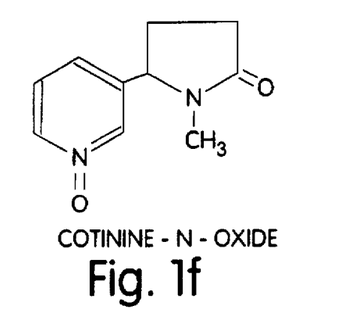
Figure 1G:
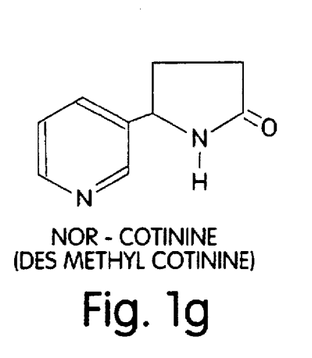
Figure 1H:
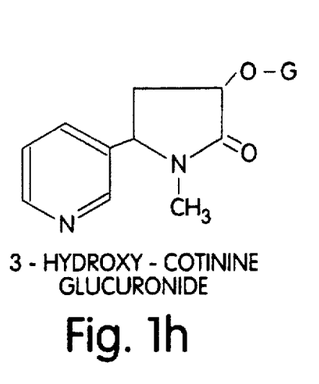
Figure 1I:
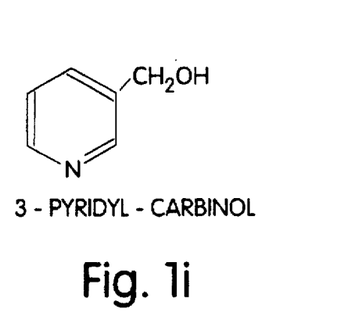
Figure 1J:
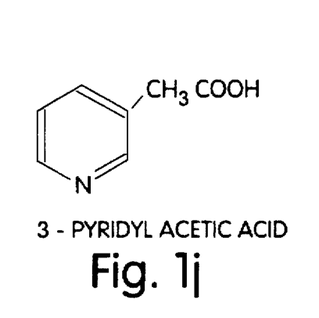
Figure 1K:
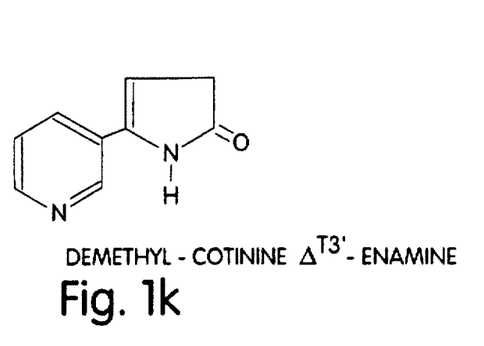
Figure 2:
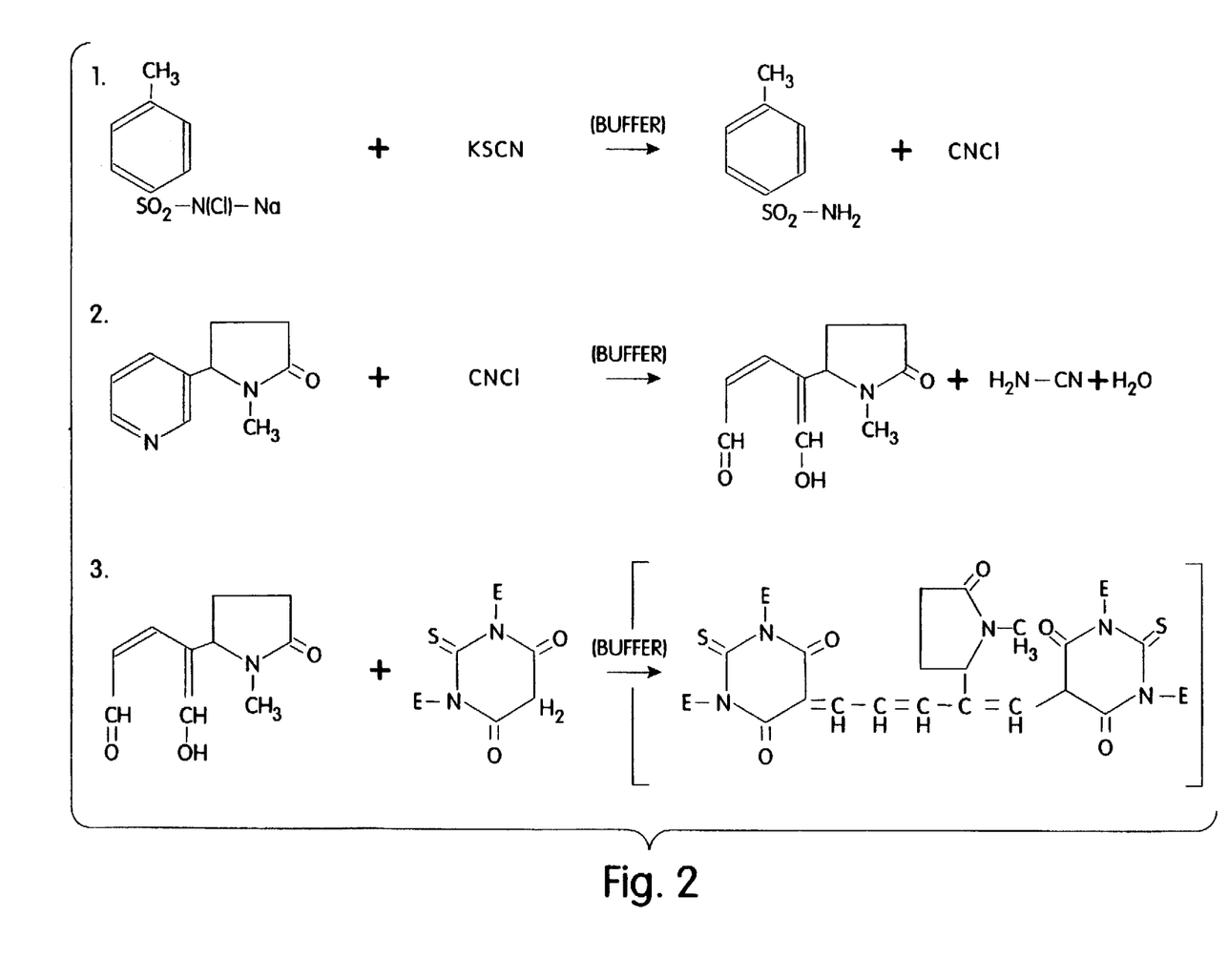
FIG. 2 depicts the reaction sequence of a nicotine metabolite, cotinine, with the preferred reagents of the assay.

The color determinant is a substance capable of producing a colored end product in the reaction assay of this invention. It is intended to include any compound which reacts with a nicotine intermediate or nicotine metabolite intermediate in the reaction assay of this invention to produce a colored end product. The nicotine intermediate or nicotine metabolite intermediate is formed as a result of a cyanogen halide forming agent reacting with a cyanogen releasing agent to form a cyanogen halide salt, which in turn reacts with the nicotine or nicotine metabolite to form the nicotine intermediate or nicotine metabolite intermediate. FIG. 2 depicts the reaction sequence of a particular nicotine metabolite, cotinine, with the preferred reagents of this invention. As shown in this reaction, the pyridine ring of cotinine is split by cyanogen chloride and condensed with the color determinant to give a colored end product. The pyridine ring in nicotine and other nicotine metabolites behaves in a similar fashion.

Examples of color determinants which can be used in this invention include dimethyl barbituric acid, barbituric acid, diethyl thiobarbiturate, 5-amino-2-naphthalene sulfonic acid, 8-amino-2-naphthalene sulfonic acid, 4,5-dihydroxy naphthalene-2,7-disulfonic acid, 7-amino-1,3-naphthalene sulfonic acid monopotassium salt, 1,4-phenylene diamine dihydrochloride, O-tolidine dihydrochloride, sulfanilic acid, sulfanilamide, 4-amino-1-naphthalene sulfonic acid, p-amino benzoic acid and 4-amino salicylic acid. The preferred color determinants are barbituate derivatives. Such derivatives include barbituric acid and compounds which are structurally similar to barbituric acid. These structurally similar compounds may be an ester form of the acid (e.g. barbituate) a salt, or may be the acid, ester, or salt substituted with at least one moiety such as a sulfur or an alkyl group. Examples of barbituate derivatives include dimethyl barbituric acid, barbituric acid and diethyl thiobarbiturate. The preferred barbiturate derivative is diethyl thiobarbiturate. (Aldrich Chemical Co., Inc., Milwaukee, Wis.). The concentration of the color determinant may be selected to optimize the intensity of the color of the end product resulting from the assay reaction of this invention. The selection of a concentration of a particular color determinant is interdependent with the concentration of the other assay reagents. For example, a particular concentration of an assay reagent may be fixed to the solid phase and the concentrations of the other assay reagents may be optimized by varying the concentration until a desirable, detectable color is produced at a selected pH.

The term buffer is intended to include any substance over a range of pH values which resists a change in pH when a given increment of $H^+$ or $OH^-$ is added. The presence of a buffer in the reaction assay of this invention permits the assay of samples having a wide range of pH values. Unprocessed urine samples typically have a pH between about 4.8 and about 8.2. In testing urine samples, a buffer is selected so that test samples with pH values between about 4.8 and about 8.2 can be effectively assayed. This invention thus permits detection of nicotine and/or nicotine metabolites in an unprocessed urine sample. It should be understood that the type of buffer and the pH of the buffer may be selected based upon such factors as its ability to perform its intended function at a particular pH of the urine. Some buffers, e.g. phosphates, are more appropriate for use with urine samples having high pH's, approximately 8, while others, e.g. aconitate, are more appropriate for use with urine samples having lower pH's, approximately 4.0. Further, the particular pH of the buffer also may be manipulated by one of ordinary skill in the art. Typically, buffers having pH's of less than about 3.5 or greater than about 10 are not as useful as those having a more intermediate pH. For example, some color is observed at all pH's but a pH between 4.1 and about 4.2 is preferred for the citrate buffer. Examples of buffers which may be used in this invention include citrate buffer, acetate buffer, citrate-phosphate buffer, succinate buffer, aconitate buffer, phosphate buffer and carbonate buffer. Examples of molarities and pH values of these buffers which may be used in this invention are listed in Table 1.

TABLE 1

| Buffer | Molarity | pH |
|---|---|---|
| Citrate | 2M | 4.20 |
| | | 4.43 |
| | | 4.55 |
| | | 4.75 |
| | | 4.94 |
| | | 5.10 |
| Acetate | 4M | 4.33 |
| | | 4.63 |
| | | 4.88 |
| | | 5.13 |
| | | 5.36 |
| Citrate- | Final Conc. | 4.30 |
| Phosphate | 1M Citric Acid | 4.56 |
| | 2M Phosphate (Dibasic $Na_2HPO_4$) | 5.10 |
| Succinate | 0.5M Succinate | 3.8 |
| | | 4.5 |
| | | 5.2 |
| Aconitate | 0.05 M | 4.50 |
| | | 4.95 |
| | | 5.30 |
| | | 5.95 |
| Phosphate | 0.1M | 5.7 |
| | | 6.5 |
| | | 7.0 |
| | | 8.0 |
| Carbonate | 0.1M | 9.2 |
| | | 10.0 |
| | | 10.7 |

For the system described in the examples, the preferred buffer is citrate buffer. The preferred molarity of the citrate buffer is 2M. The preferred pH of the citrate buffer is between about 4.1 and about 4.2.

The term cyanogen releasing agent is intended to include any compound which provides cyanogen in a reaction with a particular cyanogen halide forming agent to produce a cyanogen halide salt. Examples of a cyanogen releasing agent which may be used in this invention include potassium thiocyanate, sodium thiocyanate, potassium cyanide and sodium cyanide. The preferred cyanogen releasing agent is potassium thiocyanate. (Aldrich Chemical Co., Inc., Milwaukee, Wis.).

The term cyanogen halide forming agent is intended to include any compound which provides a halide in a reaction with a particular cyanogen releasing agent to produce a cyanogen halide salt. Examples of a cyanogen halide forming agent which may be used in this invention include chloramine-T and chloramine-B. The preferred cyanogen halide forming agent is chloramine-T. (Aldrich Chemical Co, Inc., Milwaukee, Wis.).

The solid phase contains reagents necessary to detect nicotine and/or nicotine metabolites. The term contains is intended to include any application of a reagent onto the solid phase which, after drying, results in the reagent being located on or within the solid phase. Examples of containing include impregnation, adsorption, absorption and the like.

The reagents may be applied to the solid phase so that they are arranged in a sequence which maximizes production of the end product in the color reaction assay. The preferred sequences are: (1) color determinant, buffer, cyanogen releasing agent and cyanogen halide forming agent, or (2) color determinant, cyanogen releasing agent, buffer and cyanogen halide forming agent. In either of these arrangements, immersion of one end of the solid phase into a liquid test sample results in the liquid initially making contact with the color determinant. The liquid then sequentially passes through the other reagents in the order that they are present on the solid phase, by capillary action. If nicotine or nicotine metabolites are present in the liquid sample, the reactions described above take place, resulting in a colored end product.

This invention also permits the detection of only nicotine and/or nicotine metabolites on a solid phase. The term only is intended to mean that the solid phase is designed for the purpose of primarily detecting the pyridine ring in nicotine and/or nicotine metabolites, and is not designed for the purpose of also detecting other chemical constituent groups present on other types of compounds. The term only, however, may include other cross-reacting compounds which contain a pyridine ring, and which are present in sufficiently high concentration. Preferably, the presence of such cross-reacting compounds is independently determined and corrected for. For example, niacin at therapeutic levels (1-2 gm ingested per day) but not at dietary supplement levels has been shown to give a positive result in the test assay of the invention. Preferably, the person being tested will disclose whether he or she has been ingesting such compounds. Alternatively, the cross-reacting compounds can be eliminated from the urine prior to contacting the urine with the solid phase. For example, an ionic resin column may be used to eliminate ionic cross-reacting compounds.

Niacin (and its metabolites) at therapeutic levels is the only drug tested by the inventors that has shown cross-reactivity with a color reaction in an assay using the strip described in the examples below. Other drugs tested with negative cross-reactivity are set forth in Tables 2a and 2b below. The compounds in Table 2a were tested for cross-reactivity with the strip described in the examples below at a concentration of 100,000 ng/ml unless otherwise noted.

Table 2a

*Alcohol
*Benzodiazepines
*Cocaine/Metabolites
*Marijuana
*Methadone
*Opiates (Morphine, Heroine)
Acetamiophen
Alprazolam
Amitriptyline
Amobarbital
Amoxicillin
Asp-Phe-methylester (aspartame)
Atenolol
Atropine Sulfate
AZT (3' Azido-3'-Deoxythymidine)
Barbital
Benzilic acid β-diethyl-aminoethyl ester
Benzoylecgonine
Brompheniramine
Bupivacaine
Buspirone
Butethal
Caffeine
Cephaloridine
Chloramphenicol
Chloroquine
Chlorpheniramine
Chlorpromozine
Chlorpropamide
Chlorthiazide
Chlorzoxazone
Cimetidine
Ciprofloxacin
Clemastine
Clindamycin
Clonidine
Cocaine HCl
Codeine
Codeine Sulfate
Cortisone
Cyclizine
Cyclobenzaprine
Cyproheptadine
Desmethylydiazepam
Dextromethorphan
Diazepam
Dibucaine
Digaxin
Diphenhydramine
Diphenoxylate
Dipyridamole
Doxylamine
Ephedrine Sulfate
Epinephrine
***Fenoprofen
Fentanyl
5-Hydroxyindole-3-acetic acid
5-Hydroxyindole-2-carboxylic acid
5-(p-hydroxyphenyl)-5-phenylhydentoine
5-Hydroxytryptamine
5-Pregnen-3 ol-20-one, acetate
Flurazepam
Flurbiprofen
Furosemide
4-Dimethylaminopyrine
Glutethimide Guaiaco glyceryl ether
Haloperidol
Hippuric acid
Histamine
Hydralazine
Hydrochlorothiazide
Hydroxyzine
I-Amphetamine
\*\*\*\*Ibuprofen
Indole-3-butyric acid
Indomethacin
Iproniazid
Ketoprofen
Labetalol
\*\*\*\*Loperamide
Meprobamate
Methadone
Methadone HCl
Methamphetamine
Methapyrilene
Methsuximide
Methyprylon
Metrondazole
Methylphenidate
Morphine Sulfate
Morphine-3-β-D-Glucuronide
Nalidixic acid
Naphazoline HCl
\*\*Naproxen
Nifedipine
Norethindrone
Norfloxacin
n-norpropoxyphene
Nortriptyline
Nortryptaline
Orotic Acid
Oxazepam
Oxymetazoline
Pemoline
Penicillin G
Pentobarbital
\*\*Pheniramine, maleate
Phencyclidine
Phenmethazine
Phenobarbital
Phenylpropanolamine
Pheobarbital
Piroxicam
Prazosin
Procaine HCl
Promethazine
Propanolol
Propoxyphene
Pseudo-ephedrine
Quinidine, HCl
Ranitidine, HCl
Secobarbital
Sulfamethoxazole
Tetrahydrozoline
Triprolidine, HCl
Tryptamine \*Urine samples from drug abusers.
\*\*No cross-reactivity at 50,000 ng/ml.
\*\*\*Tested at 500,000 ng/ml
\*\*\*\*Tested at 1,000,000 ng/ml TABLE 2b Over-the-Counter Drugs That Were Found to Have No Cross-Reactivity With the Reagent Impregnated Test Strip

| Brand Name | Use |
| --- | --- |
| 1. Vicks Formula 44-D Syrup | Cough Syrup |
| 2. Cepacol (New) | Dry Throat Lozenges |
| 3. Cepacol (Original) | Dry Throat Lozenges |
| 4. Actifed (Tablets) | Head Cold and Allergy |
| 5. Triaminicol Syrup | Multi-Symptom, Relief, Cough, Cold, Runny Nose |
| 6. CVS Sore Throat Lozenges | Sore Throat |
| 7. Surbex-T | Treatment of Vitamin Deficiency |
| 8. Dimetapp Extent-Tablets | Anti-Histamine, Nasal Decongestant |
| 9. Benylin Syrup | Cough |
| 10. Tylenol Extra Strength Gel Cap | Pain Relief |
| 11. Chloraseptic Spray Advanced Formula | Sore Throat |
| 12. Advil | Pain Killer |
| 13. Peptobismol Tablets | Upset Stomach |
| 14. CVS Nasal Decongestant Tablets | Nasal Decongestant |
| 15. Chloraseptic Tablets | Sore Throat |
| 16. Tylenol Allergy Sinus | Analgesic, Decongestant, Anti-Histamine |
| 17. Sine-Aid | Sinus Headache |
| 18. Dexatrim | Weight Loss |
| 19. Buffered Aspirin | Analgesic |
| 20. Mygranil | \*Prescription for Migraine |

Volunteers were given the drug at doses as prescribed on the package and urine samples were collected at 2-4 hour intervals for a total of 24 hours from the time of ingestion of first dose.

This invention also pertains to a method for detecting nicotine and/or nicotine metabolites in a liquid sample. This method entails contacting the liquid sample with a solid phase impregnated with assay reagents including a color determinant, a buffer, a cyanogen releasing agent and a cyanogen halide forming agent, and detecting the formation of color as indicative of the presence of nicotine and/or nicotine metabolites. The terms nicotine and/or nicotine metabolites, solid phase, impregnated, color determinant, buffer, cyanogen releasing agent and cyanogen halide forming agent are used as defined above.

The term contacting is intended to include any procedure whereby the solid phase makes physical contact with the liquid sample. Examples of ways in which contact can be made include immersing, either manually or mechanically, the solid phase into a container which contains the liquid sample, or applying an aliquot of the liquid sample onto the solid phase. Preferably, one end of the solid phase is immersed into the liquid sample, such that the liquid initially makes contact with the color determinant. Then, by capillary action, the liquid sample moves through the solid phase, sequentially making contact with the buffer, the cyanogen releasing agent and the cyanogen halide forming agent, or, sequentially making contact with the cyanogen releasing agent, the buffer and the cyanogen halide forming agent.

In order to achieve advantages of the invention, the amount of sample applied to the strip and the manner in which the sample is applied to the strip are specified. It is preferable that the sample be contacted with only a portion of the strip, with capillary action drawing the sample through the strip and into contact with the various reagents of the strip. In the preferred strip (see examples), the end of the strip containing the color determinant is immersed in the sample with approximately ½ of the color determinant region being immersed. The remaining portions of the strip are not immersed. Also in the preferred assay (see examples), a sample of about 0.5 ml is contacted with the color determinant end of the strip. This is a sufficient volume to permit the sample to contact the reagents such that a color end product is produced, but not so much for example to reduce color intensity due to dilution, to reduce the effects of the buffer due to dilution, or to cause any of the reagents to be washed from the strip.

The term detecting the formation of color is intended to include any process whereby the presence or absence of color is determined. Such processes include visual detection and detection with instruments. The preferred method for detecting color formation is visual detection. The formation of color can be detected on the solid phase or in the liquid test sample. Preferably, color is detected on the solid phase. Depending upon the color determinant that is selected for the reaction assay, a particular color is formed if nicotine and/or nicotine metabolites are present in the test sample. When the preferred color determinant, diethyl thiobarbiturate, is used in the reaction assay, the presence of nicotine and/or nicotine metabolites in the test sample results in the formation of a pink color. The assay of this invention can be used as a qualitative assay, in that the formation of any color indicates the presence of nicotine and/or nicotine metabolites. The assay of this invention can also be used as a semi-quantitative or quantitative assay, in that the intensity of color formed on the solid phase is indicative of the amount of nicotine and/or nicotine metabolites present in the test sample. This would be desirable for distinguishing between a light or heavy smoker. Preferably, the intensity of color formation from the reaction assay is compared to a standard in which a known quantity of nicotine and/or nicotine metabolites has been contacted with a duplicate solid phase. The term duplicate solid phase is intended to include a solid phase that is essentially identical to the solid phase used in the reaction assay for the test sample, in terms of composition, size, shape and the impregnated reagents. The standard may be generated by performing an assay reaction with a solution containing a known concentration of nicotine and/or nicotine metabolites. The standard may also be a reference color chart which is generated to simulate the intensity of color formed when an assay reaction with a solution containing a known concentration of nicotine and/or nicotine metabolites is performed. For example, a standard representing 5–6 µg/ml and 12–15 µg/ml of nicotine and/or nicotine metabolites in urine can be used to identify light to moderate and heavy smokers, respectively. A negative control with 0 µg/ml of nicotine and/or nicotine metabolites also may be included. Alternatively, a semi-quantitative or quantitative determination of nicotine and/or nicotine metabolites may be made by measuring the optical densities in a spectrophotometer of the liquid test samples themselves, which also turn color as a result of the solid phase of this invention being immersed into the liquid test samples.

The method of this invention is capable of assaying unprocessed urine from smokers for the presence of nicotine and/or nicotine metabolites. This invention is also capable of assaying urine for the presence of nicotine and/or nicotine metabolites from nonsmokers who have been exposed to secondary smoke inhalation/ingestion if their urine sample is concentrated prior to the assay reaction. The urine may be concentrated using any art-recognized concentration protocol. For example, the urine may be concentrated using an XAD-2 resin column as descibed in Mule et al. *Journal of Chromatography*, 63 (1971) p289–301; Yamasaki et al. *PNAS* 74 (1977) p3555–3559; Kullberg et al. *Clin. Chem.* 20 (1974) pp 177–183; Kullberg et al. *Biochemical Medicine* 7 (1973) pp 323–335; and Miller et al. *Biochemical Medicine* 7 (1973) pp 145–158. The contents of each of the references are hereby expressly incorporated by reference.

This invention further pertains to a method for preparing a solid phase for detecting nicotine and/or nicotine metabolites. The method involves applying the assay reagents, including a color determinant, a buffer, a cyanogen releasing agent and a cyanogen halide forming agent onto the solid phase, and drying the solid phase containing the applied reagents. The terms solid phase, nicotine and/or nicotine metabolites, color determinant, buffer, cyanogen releasing agent and cyanogen halide forming agent are used as defined above.

The term applying is intended to include any process whereby the reagents result in being impregnated, adsorbed, or absorbed onto or within the solid phase. Application of the reagents can be accomplished manually or mechanically. Preferably, the reagents are applied such that the reagents are arranged in the particular sequences previously discussed. The term drying is intended to include air drying and any type of mechanical drying process.

Preferably, the dried solid phase is packaged in a moisture proof material preferably formed into sleeves or pouches. A moisture proof material is desirable because moisture is an important factor in decreasing the stability of the reagent impregnated strip. Examples of moisture proof material include polypropylene coated aluminum foil, polypropylene and polyethylene.

Figure 3:
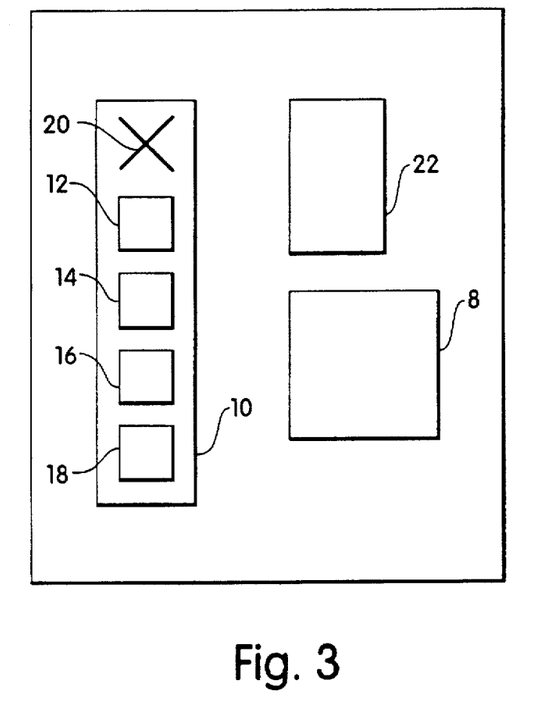
FIG. 3 depicts a kit including a package containing a solid phase impregnated with reagents including a color determinant, a buffer, a cyanogen releasing agent and a cyanogen halide forming agent, and instructions.

This invention further pertains to kits useful for detecting nicotine and/or nicotine metabolites. The kits contain a solid phase according to the invention, as well as instructions for use. For example, the kit, as shown in FIG. 3, contains instructions (8). The kit may also contain at least one packaged strip (10) impregnated with the assay reagents in the order chloramine-T (12), potassium thiocyanate (14), citrate buffer (16) and diethyl thiobarbiturate (18), and labelled on the top of the strip with a mark (20). There may be a box containing multiple individually packaged strips. The kit may also contain a color chart (22) which corresponds to a number of positive control colors. For example, one color might correspond to the color formed in the assay from a urine sample of a light smoker, and another color might correspond to the color formed in the assay from a urine sample of a heavy smoker. Alternatively, the kit may contain at least one standard solution of nicotine and/or nicotine metabolites at a known concentration. These solutions may be used to obtain strips with a given intensity of color to be used as comparisons for the test assays.

The following nonlimiting examples further illustrate the present invention.

EXAMPLE 1

Preparation of Paper Strips

Absorbent Paper Grade #222 (Ahlstrom Filtration Co., Mount Holly Springs, Pa.) was cut to 7.5×25 cm size with letters "DG→" printed at 0.5 cm intervals along the length of the strip with an arrow pointing to the bottom of the 7.5 cm length.

This paper was then cut to 0.5×7.5 cm size strips using a sharp razor blade in a strip cutter. Only strips with sharp edges were used.

EXAMPLE 2

Preparation and Application of Reagents to Paper Strips

40% chloramine-T was prepared by dissolving 40 gm of chloramine-T in warm water to make 100 ml final volume. This solution was kept warm at 65°–70° C. during dispensing. 100% potassium thiocyanate was prepared by dissolving 100 gm of potassium thiocyanate in water to make a final volume of 100 ml, while shaking under warm tap water. 2M citrate buffer was prepared by combining 23 ml of 2M citric acid with 27 ml of 2M trisodium citrate to give a pH of 4.2. 2.5% diethyl thiobarbiturate was prepared by dissolving 2.5 gm of diethyl thiobarbiturate in 100–80% ethanol to a final volume of 100 ml.

The blank strips from Example 1 were arranged on a strip support provided with shallow grooves to hold strips in place, with all the 'DG→' facing one side. Using an eight channel multipipetter, the reagents were applied onto the strips starting with chloramine-T, followed by potassium thiocyanate, citrate buffer, and finally, diethyl thiobarbiturate. The volumes of each of the reagents and the spacing of each on the strip were as follows: 40% chloramine-T—31.5 µl at the top end where 'DG→' was printed; 100% potassium thiocyanate—15 µl approximately 2 cm from the top; 2M citrate buffer pH 4.2—20 µl approximately 4 cm from the top; and 2.5% diethyl thiobarbiturate—20 µl at the bottom end of the strip.

After all the reagents were dispensed onto the strips, they were transferred onto a mesh tray and dried in a box attached with an exhaust fan. To enhance the drying process, warm air was blown into the box from the opposite end of the fan. The strips were dry in one hour. Since moisture is an important factor in the stability of the strips, they were generally dried for longer than 1½ hours.

EXAMPLE 3

Packaging of Paper Strips

After the paper strips were dried, they were packaged individually in a moisture proof material such as polypropylene coated aluminum foil, polypropylene or polyethylene. The strips were packaged in small numbers, e.g., in sets of 5 per sleeve, each strip in its own pouch. Perforations were made between individual pouches so that single strips could be used without affecting the rest of the strips. On the side of the box containing the above package, a panel of colors was included to indicate one negative and two positive control colors. One of the positive colors corresponded to light to moderate smoker urine and the second color corresponded to heavy smoker urine. The packaged strips remain stable in the original packaging for at least a year at refrigerator temperature.

EXAMPLE 4

Use of Paper Strips for Assaying Urine Samples for the Presence of Nicotine and Nicotine Metabolites Approximately 0.5 ml of urine was pipetted into a 13×100 mm tube. The package containing the reagent impregnated paper strip was cut open at the top and the strip was taken out with forceps and dropped into the urine sample with the arrow pointing downwards. It was allowed to stand for 10–15 minutes, and any color changes were observed. Urine containing no nicotine or nicotine metabolites did not change the color of the strip. The presence of nicotine and its metabolites in a urine sample gave a pink color, both on the strip and in the solution. The presence or absence of cotinine a nictone/metabolite was independently verified using an enzyme immunoassay (EIA). The color was stable for almost an hour, after which it started to fade. Closing the tubes with a cap improved the final color intensity slightly.

EXAMPLE 5

EIA Assays From the Urine of a Person Smoking One Cigarette

EIA assays were performed as described in Djercke et al., *The Journal of Immunological Methods*, 90, (1986), pp. 203–213, the contents of which is expressly incorporated by reference on urine samples taken at various times from a person who had smoked one cigarette.

TABLE 3

| Time Elapsed After Smoking | Reagent Impregnated Paper Strip Test | EIA Cotinine (µg/ml) |
|---|---|---|
| 0 hours | − | 0.0 |
| 3 hours | − | 0.023 |
| 4 hours | + | 0.160 |
| 5½ hours | + | 0.120 |

EXAMPLE 6

Comparison of Paper Strip and EIA Assays

The urine from 8–10 nonsmokers, light smokers, moderate smokers and heavy smokers was tested for the presence of nicotine and/or nicotine metabolites. Paper strip assays were performed as described in Example 4, and EIA assays were performed as described in Example 5.

TABLE 4

| | Reagent Impregnated Paper Strip Test | EIA Cotinine (µg/ml) |
|---|---|---|
| I. Non-Smokers | | |
| 1 | — | 0.08 |
| 2 | — | 0.12 |
| 3 | — | 0.028 |
| 4 | — | *0.07 |
| 5 | — | N.D. |
| 6 | — | *0.07 |
| 7 | — | 0.0 |
| 8 | — | 0.0 |
| (4/8 Subjects Self-Reported Consumption of 3–5 Cigarettes/Day) | | |
| II. Light Smokers | | |
| 1 | L | 0.7 |
| 2 | L | 2.2 |
| 3 | L | 0.64 |
| 4 | L | 0.20 |
| 5 | L | 2.00 |
| 6 | L | 1.2 |
| 7 | L | 0.7 |
| 8 | L | 1.4 |

TABLE 4-continued

|   | Reagent Impregnated Paper Strip Test | EIA Cotinine (μg/ml) |
| --- | --- | --- |
| (6/9 Subjects Self-Reported Consumption of 1 Pack/Day) | | |
| III. Moderate Smokers | | |
| 1 | M | 1.0 |
| 2 | M | 2.3 |
| 3 | M | 1.1 |
| 4 | M | N.D. |
| 5 | M | 1.1 |
| 6 | M | 1.6 |
| 7 | M | 1.4 |
| 8 | M | 2.0 |
| 9 | M | 2.3 |
| (8/10 Subjects Self-Reported Consumption of 1–2 Packs/Day) | | |
| IV. Heavy Smokers | | |
| 1 | H | 4.0 |
| 2 | H | 7.6 |
| 3 | H | 4.0 |
| 4 | H | 2.1 |
| 5 | H | 3.7 |
| 6 | H | 2.6 |
| 7 | H | 2.5 |
| 8 | H | 3.2 |
| 9 | H | 5.6 |
| 10 | H | 8.0 |

*known secondary smoke exposure
L = light; M = moderate; and H = heavy
The L, M, and H designations were determined by observing the intensity of the pink color.

EQUIVALENTS

Those skilled in the art will be able to ascertain, using no more than routine experimentation, many equivalents of the specific embodiments of the invention described herein.

These and all other equivalents are intended to be encompassed by the following claims.

We claim:

1. A method for detecting nicotine metabolites in urine comprising:
   a) contacting a solid support with urine, said solid support having a porous matrix, and said porous matrix having a receiving section and a wicking section, said receiving section for contacting urine and said wicking section for receiving urine through capillary action from said receiving section to define a flow of fluid, said porous matrix impregnated with reagents, said reagents comprising a color determinant, a buffer, a cyanogen releasing agent and a cyanogen halide forming agent; said buffer, said cyanogen releasing agent and said cyanogen halide forming agent contained in said wicking section; each of said reagents occupying a separate and distinct area of the matrix to prevent interactions between said reagents, said areas being located relative to one another in an order defined by the flow of liquid in the porous matrix in which the first reagent to come in contact with urine is said color determinant and the last reagent to come in contact with urine is said cyanogen halide forming agent; said porous matrix absorbing urine in the receiving section and wicking liquid through the wicking section to bring said cyanogen releasing agent and cyanogen halide forming agent together to form a first reaction product in the presence of said buffer, which buffer maintains said first reaction product within a pH range; said first reaction product reacts with nicotine and nicotine metabolite, if present, to form a second reaction product, said second reaction product is maintained with a pH range by said buffer; said second reaction product reacting with said color determinant to form a third reaction product, which third reaction product is maintained within a ph range by said buffer, and is detectable by a change in color; and
   b) monitoring said solid support for a change in color indicative of the presence of nicotine and nicotine metabolites.

2. The method of claim 1 wherein said buffer has a buffer capacity to maintain said liquid in said porous matrix at a pH between 5–6 in urine samples having a pH of 4.8–8.2.

3. The method of claim 1 wherein said buffer is selected from the group consisting essentially of citrate buffer, acetate buffer, citrate-phosphate buffer, succinate buffer, aconitate buffer, phosphate buffer and carbonate buffer.

4. The method of claim 1 wherein said buffer is citrate buffer.

5. The method of claim 1 wherein said cyanogen releasing agent is selected from the group consisting of potassium thiocyanate, sodium thiocyanate, potassium cyanide, and sodium cyanide.

6. The method of claim 1 wherein said cyanogen releasing agent is potassium thiocyanate.

7. The method of claim 1 wherein the color determinant is a barbiturate derivative.

8. The method of claim 1 wherein the color determinant is selected from the group consisting of barbituric acid, dimethyl barbiturate, diethyl thiobarbiturate, 5-amino-2-naphthalene sulfonic acid, 8-amino-2-naphthalene sulfonic acid, 4,5-dihydroxy naphthalene-2,7-disulfonic acid, 7-amino-1,3-naphthalene sulfonic acid monopotassium salt, 1,4-phenylene diamine dihydrochloride, 0-tolidine dihydrochloride, sulfanilic acid, sulfanilamide, 4-amino-1-naphthalene sulfonic acid, p-amino benzoic acid and 4-amino salicylic acid.

9. The method of claim 1 wherein the color determinant is diethyl thiobarbiturate.

10. The method of claim 1 wherein the color determinant is methyl barbituric acid or barbituric acid.

11. The method of claim 1 wherein the cyanogen halide forming agent is selected from the group consisting of chloramine-T and chloramine-B.

12. The method of claim 1 wherein the cyanogen halide forming agent is chloramine-T.

13. The method of claim 1 wherein the solid phase is a strip of paper.

14. The method of claim 1 wherein the solid phase is selected from the group consisting of cellulose, fiberglass and tuff glass.

15. A solid support, for detecting nicotine and nicotine metabolites in urine, comprising:
   a porous matrix, said porous matrix having a receiving section and a wicking section, said receiving section for contacting urine and said wicking section for receiving urine through capillary action from said receiving section to define a flow of fluid, said porous matrix impregnated with reagents, said reagents comprising a color determinant, a buffer, a cyanogen releasing agent and a cyanogen halide forming agent; said buffer, said cyanogen releasing agent, and said cyanogen halide forming agent contained in said wicking section, each of said reagents occupying a separate and distinct area of the matrix to prevent interactions between said reagents, said areas being located relative to one another in an order defined by the flow of liquid in the porous matrix in which the first reagent in the flow of liquid is said color determinant and the last reagent in the flow of liquid is said cyanogen halide forming agent; said porous matrix absorbing urine in the receiving section and wicking liquid through the wicking section to bring said cyanogen releasing agent and cyanogen halide forming agent together to form a first reaction product in the presence of said buffer, which buffer maintains said first reaction product within a pH range; said first reaction product reacts with nicotine and nicotine metabolites, if present, to form a second reaction product, said second reaction product maintained within a pH range by said buffer; said second reaction product reacting with said color determination to form a third reaction product, which third reaction product is maintained within a pH range by said buffer, said third reaction product is detectable by a change in color, which change in color is indicative of the presence of nicotine and nicotine metabolites.

16. The solid support of claim 15 wherein said buffer has a buffer capacity to maintain said liquid in said porous matrix at a pH between 5–6 in urine samples having a pH of 4.8–8.2.

17. The solid support of claim 15 wherein said buffer is selected from the group consisting essentially of citrate buffer, acetate buffer, citrate-phosphate buffer, succinate buffer, aconitate buffer, phosphate buffer and carbonate buffer.

18. The solid support of claim 15 wherein said buffer is citrate buffer.

19. The solid support of claim 15 wherein said cyanogen releasing agent is selected from the group consisting of potassium thiocyanate, sodium thiocyanate, potassium cyanide, and sodium cyanide.

20. The solid support of claim 15 wherein said cyanogen releasing agent is potassium thiocyanate.

21. The solid support of claim 15 wherein the color determinant is a barbiturate derivative.

22. The solid support of claim 15 wherein the color determinant is selected from the group consisting of barbituric acid, dimethyl barbiturate, diethyl thiobarbiturate, 5-amino-2-naphthalene sulfonic acid, 8-amino-2-naphthalene sulfonic acid, 4,5-dihydroxy naphthalene-2,7-disulfonic acid, 7-amino-1,3-naphthalene sulfonic acid monopotassium salt, 1,4-phenylene diamine dihydrochloride, 0-tolidine dihydrochloride, sulfanilic acid, sulfanilamide, 4-amino-1-naphthalene sulfonic acid, p-amino benzoic acid and 4-amino salicylic acid.

23. The solid support of claim 15 wherein the color determinant is diethyl thiobarbiturate.

24. The solid support of claim 15 wherein the color determinant is methyl barbituric acid or barbituric acid.

25. The solid support of claim 15 wherein the cyanogen halide forming agent is selected from the group consisting of chloramine-T and chloramine-B.

26. The solid support of claim 15 wherein the cyanogen halide forming agent is chloramine-T.

27. The solid support of claim 15 wherein the porous matrix is paper.

28. The solid support of claim 15 wherein the porous matrix is selected from the group consisting of cellulose, fiberglass and tuff glass.

29. The solid support of claim 15 consisting essentially of the porous matrix, the color determinant, the buffer, the cyanogen releasing agent and the cyanogen halide forming agent.

30. A method for detecting nicotine metabolites in urine comprising:

a) contacting a cellulose paper solid support with urine, said solid support having a porous matrix, and said porous matrix having a receiving section and a wicking section, said receiving section for contacting urine and said wicking section for receiving liquid through capillary action from said receiving section to define a flow of fluid, said porous matrix impregnated with reagents, said reagents comprising a color determinant, a citrate buffer, a cyanogen releasing agent and a cyanogen halide forming agent said buffer, said cyanogen releasing agent and said cyanogen halide forming agent contained in said wicking section; each of said reagents occupying a separate and distinct area of the matrix to prevent interactions between said reagents, said areas being located relative to one another in an order defined by the flow of liquid in the porous matrix in which the first reagent to come in contact with urine is said color determinant and the last reagent to come in contact with urine said cyanogen halide forming agent; said porous matrix absorbing urine in the receiving section and wicking liquid through the wicking section to bring said cyanogen releasing agent and cyanogen halide forming agent together to form a first reaction product in the presence of said citrate buffer, which citrate buffer maintains said first reaction product within a pH range of between 5–6 in urine samples having a pH of 4.8–8.2; said first reaction product reacts with nicotine and nicotine metabolites, if present, to form a second reaction product, said second reaction product is maintained within said pH range by said citrate buffer; said second reaction product reacting with said color determinant to form a third reaction product, which third reaction product is maintained within said pH range by said citrate buffer and is detectable by a change in color, said color determinant selected from the group consisting of diethyl thiobarbituric acid and barbituric acid, said cyanogen releasing agent selected from the group consisting of potassium thiocyanate and sodium thiocyanate, and said cyanogen halide forming agent selected from the group consisting of chloramine-T and chloramine-B; and b) monitoring said solid support for a change in color indicative of the presence of nicotine and nicotine metabolites.

* * * * *